United States Patent [19]

Dunn

[11] Patent Number: 4,816,473
[45] Date of Patent: * Mar. 28, 1989

[54] AROYL BENZOFURAN AND BENZOTHIOPHENE ACETIC AND PROPIONIC ACIDS

[75] Inventor: James P. Dunn, Los Altos, Calif.

[73] Assignee: Syntex (U.S.A.) Inc., Palo Alto, Calif.

[ * ] Notice: The portion of the term of this patent subsequent to Oct. 25, 2005 has been disclaimed.

[21] Appl. No.: 910,118

[22] Filed: Sep. 22, 1986

Related U.S. Application Data

[63] Continuation of Ser. No. 719,662, Apr. 3, 1985, abandoned, which is a continuation of Ser. No. 513,545, Jul. 14, 1983, abandoned.

[51] Int. Cl.$^4$ .................... A61K 31/38; C07D 333/52
[52] U.S. Cl. ...................... 514/443; 514/444; 514/467; 514/469; 549/51; 549/57; 549/60; 549/448; 549/462; 549/471
[58] Field of Search .............. 549/57, 51, 468, 60, 549/448, 462, 471; 514/443, 444, 467, 469

[56] References Cited

U.S. PATENT DOCUMENTS

| | | |
|---|---|---|
| 2,930,800 | 3/1960 | Kloetzel et al. . |
| 3,558,655 | 1/1971 | Kaltenbronn . |
| 3,598,839 | 8/1971 | Kaltenbronn . |
| 3,682,976 | 8/1972 | Kaltenbronn . |
| 3,706,767 | 12/1972 | Kaltenbronn . |
| 3,963,758 | 6/1976 | Pinhas . |
| 4,013,692 | 3/1977 | Scherrer . |
| 4,060,528 | 11/1977 | Janssen et al. . |
| 4,126,625 | 11/1978 | Yoshina et al. . |
| 4,138,397 | 2/1979 | Bohme . |
| 4,198,519 | 4/1980 | Goudie . |
| 4,213,998 | 7/1980 | Witiak et al. . |
| 4,230,624 | 10/1980 | Le Corre et al. . |

FOREIGN PATENT DOCUMENTS

| | | |
|---|---|---|
| 874450 | 6/1979 | Belgium . |
| 8752 | 3/1980 | European Pat. Off. . |
| 2108932 | 8/1972 | Fed. Rep. of Germany . |
| 2256004 | 5/1973 | Fed. Rep. of Germany . |
| 59-51275 | 3/1984 | Japan . |
| 6912402 | 2/1970 | Netherlands . |

OTHER PUBLICATIONS

Proc. Am. Soc. Hort. Sci. 84:259–62 (1964).
J. Med. Chem. 8(5), 598–603 (1965).
Nippon Kagaku Zasshi 88(4), 445–7 (1967).
Australian J. Biol. Sci. 10, 80–4 (1957).

*Primary Examiner*—Alan Siegel
*Attorney, Agent, or Firm*—David A. Lowin; Tom M. Moran; Annette Moore

[57] ABSTRACT

Novel aroyl-substituted benzofuran and benzothiophene acetic and propionic acids are disclosed herein. These compounds are useful as analgesic, anti-inflammatory, and antipyretic agents.

16 Claims, No Drawings

AROYL BENZOFURAN AND BENZOTHIOPHENE ACETIC AND PROPIONIC ACIDS

This is a continuation of U.S. Ser. No. 719,662 filed Apr. 3, 1985 now abandoned which is a continuation of U.S. Ser. No. 513,545 filed July 14, 1983 now abandoned, incorporated herein by reference.

SUMMARY OF THE INVENTION

The present invention relates to certain novel substituted benzofuran and benzothiophene alkyl acid compounds. More particularly, this invention relates to benzofuran-5-yl acetic and propionic acid and benzothiophen-5-yl acetic and propionic acid compounds optionally substituted at position 6 and containing an aroyl substituent at position 7. This invention also covers the 2,3 dihydro analogs of the aforementioned compounds all of which are represented by Formula I or a pharmaceutically acceptable salt

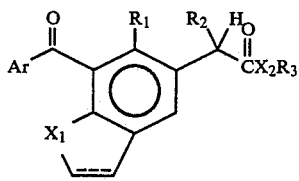

and the individual (l) and (d) isomers of the propionic acid or propionate compounds, wherein
$R_1$ is hydrogen, hydroxy, lower alkoxy or methyl;
$R_2$ is hydrogen or methyl;
$R_3$ is hydrogen, alkyl, phenyl, phenyl lower alkyl, 2-furyl, 3-furyl, 2-thienyl, 3-thienyl,

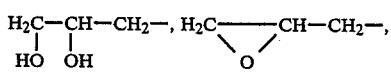

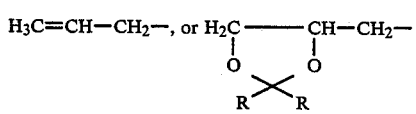

wherein the
R groups are the same and are lower alkyl;
$X_1$ is oxygen or is sulfur if $R_1$ is hydrogen;
$X_2$ is oxygen or sulfur;
Ar is phenyl unsubstituted or independently substituted with two or more substituents which are lower alkyl, lower alkoxy, halo, lower alkylsulfinyl, lower alkylsulfonyl, lower alkylthio, 2-furyl, 3-furyl, 2-thienyl, or 3-thienyl; and the dotted line represents a single or double bond.

In a second aspect, this invention relates to a pharmaceutical composition comprising a pharmaceutically acceptable excipient in admixture with a compound according to Formula I.

A further aspect of this invention is the use of a compound according to Formula I for the treatment of analgesia, inflammation, and pyrexia in mammals which method comprises administering to a mammal an effective amount of Formula I either alone or in admixture with a pharmaceutically acceptable excipient.

In yet a further aspect, this invention relates to a process for preparing a compound according to Formula I which process comprises:

(a) treating a compound of the formula

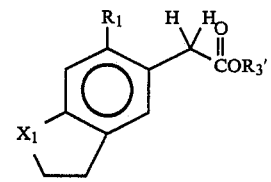

wherein $R_1$ and $X_1$ are defined hereinabove, and $R'_3$ is an ester forming group, with an aroyl acid halide; or (b) treating a compound of the formula

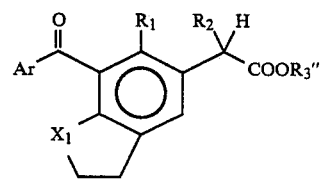

wherein Ar, $R_1$, $R_2$, and $X_1$ are defined hereinabove and $R_3''$ is hydrogen or an alkyl group, with a dehydrogenating agent; or (c) esterifying a compound of the formula:

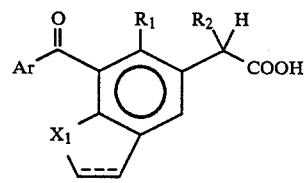

wherein Ar, $R_1$, $R_2$, and $X_1$ are defined hereinabove; or (d) alkylating a compound of the formula:

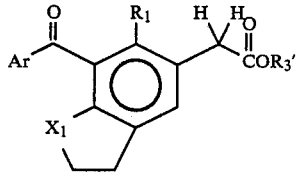

wherein Ar, $R_1$ and $X_1$ are as defined above and $R_3'$ is an ester forming group, with an alkylating agent in the presence of a strong base;

(e) converting the acid of Formula I to a pharmaceutically acceptable salt; or (f) converting an ester of Formula I to the acid; or (g) converting an ester of Formula I to a salt; or (h) converting one pharmaceutically acceptable salt to another pharmaceutically acceptable salt; or (i) converting one ester to a second ester

DETAILED DESCRIPTION OF THE INVENTION

Compounds of Formula I may be broken down into two sub-groups wherein $X_1$ oxygen or sulfur within both of these sub-groups, preferred compounds are those wherein Ar is phenyl wherein phenyl is unsubstituted or independently substituted with one or more substituents which are lower alkyl, lower alkoxy, halo, lower alkylthio, lower alkylsulfinyl or lower alkylsulfonyl. More preferred are those compounds wherein both sub-groups wherein R₁ is H. Most preferred are the following compounds:

7-benzoylbenzofuran-5-ylacetic acid;
d,l-2-(7-benzoylbenzofuran-5-yl)propionic acid;
7-(4-methylthiobenzoyl)benzofuran-5-ylacetic acid;
7-(4-chlorobenzoyl)benzofuran-5-ylacetic acid;
d,l-2-(7-(4-methylthiobenzoyl)benzofuran-5-yl)propionic acid; and
d,l-2-(7-(4-chlorobenzoyl)benzofuran-5-yl)propionic acid.

Definitions

The numbering of the benzofuran and benzothiophene structure is as follows:

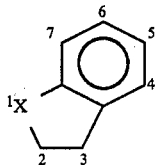

The following definitions are set forth to illustrate and define the meaning and scope of the various terms used to describe the invention herein.

As used herein, the term "alkyl" refers to a radical containing only carbon and hydrogen which is fully saturated and contains between 1 and 12 carbon atoms. Examples of such radicals are methyl, ethyl, propyl, isopropyl, butyl, t-butyl, isoamyl, pentyl, isopentyl, hexyl, octyl, nonyl, isodecyl, 6-methyldecyl and dodecyl The term "phenyl lower alkyl" refers to a radical comprising a phenyl group and having at least one methylene group but up to six methylene groups wherein the phenyl ring is attached to its designated substituent by means of the alkyl chain. Examples of phenyl lower alkyl are, benzyl, phenethyl, 3-phenylpropyl, 4-phenylbutyl, 5-phenylpentyl, and 6-phenylhexyl.

As used herein, the term "lower alkyl" refers to an alkane radical of between 1 and 6 carbon atoms and which may be a branched or straight chain radical. This term is further exemplified by such radicals as methyl, ethyl, propyl, isopropyl, butyl, t-butyl, isoamyl, pentyl, isopentyl, and hexyl.

The phrase "lower alkoxy" is to be interpreted as having the normal art meaning for the word alkoxy but herein the phrase is limited to those groups having 1 to 6 carbon atoms such as methoxy, ethoxy, propoxy, iso-propoxy, butoxy, pentoxy, hexoxy and the like.

"Halo" refers to fluoro, bromo, and chloro.

"Lower alkylthio" refers to a substituent wherein a lower alkyl chain as that term is defined hereinabove is linked to the aryl group by means of sulfur.

"Lower alkylsulfinyl" refers to a group having a lower alkyl component and wherein an —SO—, is the bridging radical between the lower alkyl group and the aryl substituent.

"Lower alkylsulfonyl" refers, as before, to a substituent wherein a lower alkyl group as defined hereinabove is linked with an aryl group by means of an —SO₂— radical.

The phenyl ring may be substituted with only hydrogen or it may be independently substituted with one or more of the several groups set forth under the definition of Ar. By independently substituted it is meant that when the ring has more than one substituent, those substituents may be the same or different. There is no limitation on the combination of multiple substitutents.

Phenyl may be substituted with a single substituent such as ethyl, methoxy, chloro, fluoro, or methylthio, for example. If the phenyl group contains only one substituent, that substituent is preferably present at position 4, the para position, though alternatively it may be present at the ortho or meta position. If phenyl has multiple substituents, it is most preferred they be of the same type but any combination of substituents may be present. The position of multiple substituents will be determined in part by the chemistry involved in their preparation. Thus, there are no special position requirements, particularly in the case of different substituents. However, positions 2, 4 and 6 would be the most frequently substituted positions for tri-substituted phenyl. It is also possible within the scope of this invention to have a penta substituted phenyl such as wherein positions 2, 3, 4, 5 and 6 are all substituted with, for example, chloro or methyl.

When R₂ is methyl and/or Ar is lower alkylsulfinyl substituted phenyl, the compounds of the present invention may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

If desired, the compounds may be resolved into their optical antipodes by conventional resolution means; for example by separation (e.g. fractional crystallization) of the diastereomeric salts formed by the reaction of these compounds with optically active acids. Any other appropriate technology may also be used to effect such a separation.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

A pharmaceutically acceptable salt may be any salt derived from an inorganic or organic base which retains the activity of the parent compound and is non-toxic to the subject. Salts may be derived from such inorganic ions as sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts pharmacetically acceptable salts derived from organic bases include salts of primary, secondary and tertiary amines, substituted amines including naturally occurring substituted amines, cyclic amines and basic ion exchange resins, such as isopropyl amine, trimethyl amine, diethyl amine, triethyl amine, tripropyl amine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylendiamine, glucosamine, methylglucamine, theobromine, purines, piperizine, piperidine, n-ethylpiperidine, polyamine resins, and the like. Particularly preferred organic bases are isopropylamine, diethylamine, ethanolamine, piperidine, tromethamine, dicyclohexylamine, choline and caffeine.

Utility and Administration

The compounds of Formula I and the pharmaceutically acceptable non-toxic esters and salts thereof, are useful as analgetic agents, anti-inflammatory agents, antipyretic agents, vasospasm inhibitors (e.g., vs migraine) platelet aggregation inhibitors, fibrinolytic agents, and as smooth muscle relaxants (e.g., for treatment of dysmenorrhea). These compounds can be used both prophylactically and therapeutically.

The compositions containing these compounds are thus useful in the treatment of pain and in the treatment and and elimination of inflammation. The compositions are also useful for treating pain which is not necessarily associated with inflammation, e.g., migraine, post-surgical pain, etc. In addition, these compositions may be used to treat other conditions such as pyrexia, platelet aggregation, relaxation of smooth muscles, vasospasms and the like.

Small animal screening tests to determine analgetic activity potential include the mouse analgetic (antiwrithing) assay according to the method of Hendershot and Forsaith, *J. Pharmacol. Exp. Ther.*, 125:237–240, (1959).

Initial small animal screening tests to determine anti-inflammatory activity potential include the carrageenin induced paw inflammation in the rat according to the method of Winter, et al., *Proc. Soc. Exp. Biol Med.*, 111:544–547, (1962) and the cotton pellet granuloma test in the rat according to the method of Meier, et al *Experientia* 6:469–471, (1950) and modifications thereof In addition, in certain cases, the anti-inflammatory activity may be evaluated by using the adjuvant arthritis assay according to the method of Pearson, *Proc. Soc. Exp. Biol. Med.*, 91:95–101, (1956). Also, in vitro tests, for example those using synovial explants from patients with rheumatoid arthritis, Dayer, et al., *J. Exp. Med.*, 145:1399–1404, (1977), are useful in determining whether compounds exhibit anti-inflammatory activity.

Generally, the antipyretic activity potential is indicated by the anti-inflammatory potential as measured by the previously mentioned assays.

Platelet aggregation inhibition potential is determined by using turbidimetric method of Born, *J. Physiol.*, (London) 162:67–68, (1962).

Potential activity as a smooth muscle relaxant is determined in vitro using the method of Vickery, *Prostaglandins Med.*, 2:299–315, (1979) or Vickery, *Prostaglandins Med.*, 2:225–235, (1979).

Administration of the active compounds of Formula I in an appropriate pharmaceutical composition can be caried out via any of the accepted modes of administration of agents for the treatment of pain, inflammation or pyrexia, or the prophylaxis thereof. Thus, administration can be for example, orally, parenterally or topically, in the form of solid, semi-solid or liquid dosage forms, such as for example, tablets, suppositories, pills, capsules, powders, solutions, suspensions, emulsions, creams, lotions, aerosols, ointments or the like, prferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 0.02 to 20 mg/kg of body weight per day of the active compound of Formula I. Most conditions respond to treatment comprising a dosage level of the order of 0.05 to 2 mg. per kilogram of body weight per day. Thus, for administration to a 70 kg person, the dosage range per day would be about 1.4 to 1400 mg per day, preferably about 3.5 to 140 mg per day.

For such oral administration, a pharmaceutically acceptable, non-toxic composition is formed by the incorporation of any of the normally employed excipients, such as, for example, pharmaceutical grades of mannitol, lactose, starch, magnesium stearate, sodium saccarine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

Generally, the pharmaceutically acceptable compositions will contain about 1% to about 90% by weight of the pharmaceutically active compound of this invention and 99% to 10% by weight of suitable pharmaceutical excipients. Preferably, the composition will be about 3.5 to 60% by weight of a pharmaceutically active compound, with the rest being suitable pharmaceutical excipients.

The active compounds of Formulas I may be formulated into a suppository using, for example, polyethylene glycols (PEG), for example, PEG 1000 (96%) and PEG 4000 (4%), as the carrier. Liquid pharmaceutically administerable compositions can, for example, be prepared by dissolving, dispersing, etc an active compound, as described above, and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pa., 16th. Edition, 1980. The composition to be administered will, in any event, contain a quantity of the active compound(s) in a pharmaceutically effective amount for relief of the particular condition being treated in accordance with the teachings of this invention.

The compounds of Formula I are also uterine smooth muscle relaxants and thus are useful as agents for maintaining the pregnancy of pregnant mammals, for the benefit of the mother and/or fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formula I are used as agents for delaying the onset of, or for postponing, parturition. As used in this application, the phrase "to delay the onset of parturition" is intended to cover that delay in parturition caused by the administration of the compounds of Formula I at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the preganancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formula I after uterine muscle contractions have begun. The condition of the patient, including the time within the gestation period when the contractions have begun, the severity of the contractions and how long the contractions have taken place will affect the results achieved with the administration of the compounds hereof. For example, the effect can be to reduce the intensity and/or the duration of the contractions (the actual act of parturition being "prolonged"), or to stop the contractions altogether. In either case, the effect will be to prolong the gestation period although, depending upon the conditions of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formula I as a uterine smooth muscle relaxant as set forth herein should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formula I or a pharmaceutical composition containing same, is administered to the pregnant mammal via any of the usual and acceptable methods known in the art. The compound can be administered either singularly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, gelatin, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition or formulation to be administered will, in any event, contain a quantity of the active compound(s) in an amount effective to delay the onset of parturition or to postpone parturition if uterine contractons have already begun. Generally a daily dose of from 0.5 mg. to about 25 mg. of the active compound per kilogram of body weight will be administered, with administration being a single daily dose or up to three or four smaller dosages regularly given throughout the day. The amount of active compound administered will, of course, depend on its relative activity.

Reaction Schemes

Those compounds of Formula I wherein $R_1$ is methyl and $X_1$ is oxygen are preliminarily prepared according to the sequence of steps set out in Reaction Scheme 1.

REACTION SCHEME 1

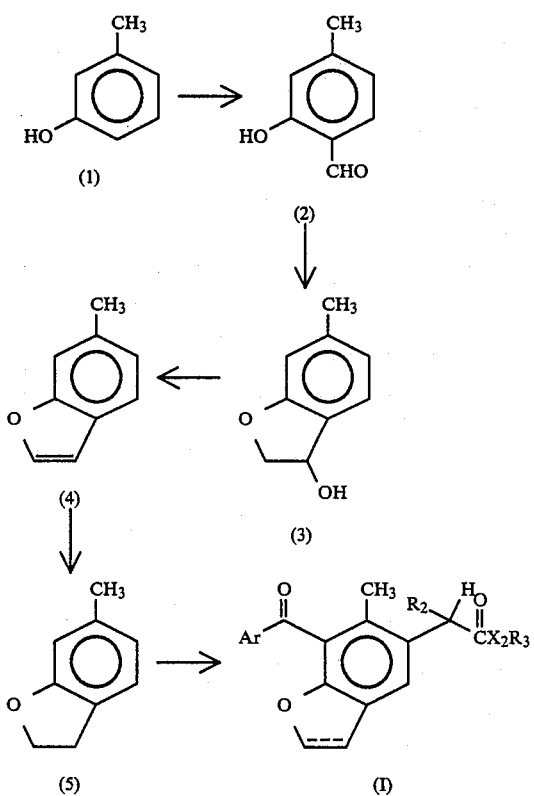

The benzaldehyde of formula 2 is prepared by the method of Caseraghl, et al in Perkin, I, pp. 1862–1865 (1980). Cresol is dissolved in a nonpolar solvent such a toluene and placed under an inert atmosphere. Tintetrachloride and tri-n-butylamine are added and the mixture stirred at between 0°–50° C., preferably ambient temperature, for about 5 to 40 minutes, preferably 20. Paraformaldehyde is then added and the solution heated to between about 50°–150° C., preferably 100° C., for up to 12 hours, preferably 8.

Preparation of the benzofuran structure, formula 3, and removal of the 2-hydroxyl radical is accomplished using the conditions of B. Holt and P. A. Lowe in Tetrahedron Letters, No 7, pp. 683–686 (1966). A solution of trimethylsulfoxonium chloride is pre-treated with sodium hydride, in an aprotic dipolar solvent, preferably tetrahydrofuran. The resultant solution is added to the 2-hydroxy-4-methylbenzaldehyde dissolved in the same solvent. This mixture is then heated at reflux for about 2 to 5 hours, preferably about 3 hours.

Removal of water to give the 6-methylbenzofuran compound is effected by refluxing a solution of the formula 3 compound with sulfuric acid in a non-polar medium such as benzene with the azeotropic removal of water. The reaction is effected in about 1 to 5 hours, usually about 3.

Reduction of the 2,3-benzofuran double bond is accomplished by catalytic hydrogenation using a transition metal catalyst such as 10% palladium on charcoal. The reaction is carried out in a simple alcohol such as ethanol under hydrogen at about 40 psi.

Following reduction, the compound of formula 5 is converted to those encompassed by Formula I by the steps set out in Reaction Scheme 4.

Reaction Scheme 2 sets out reaction steps for converting resorcinol to 2,3-dihydrobenzofuran which is then converted to the compounds of Formula I by the method set out in Reaction Scheme 4.

REACTION SCHEME 2

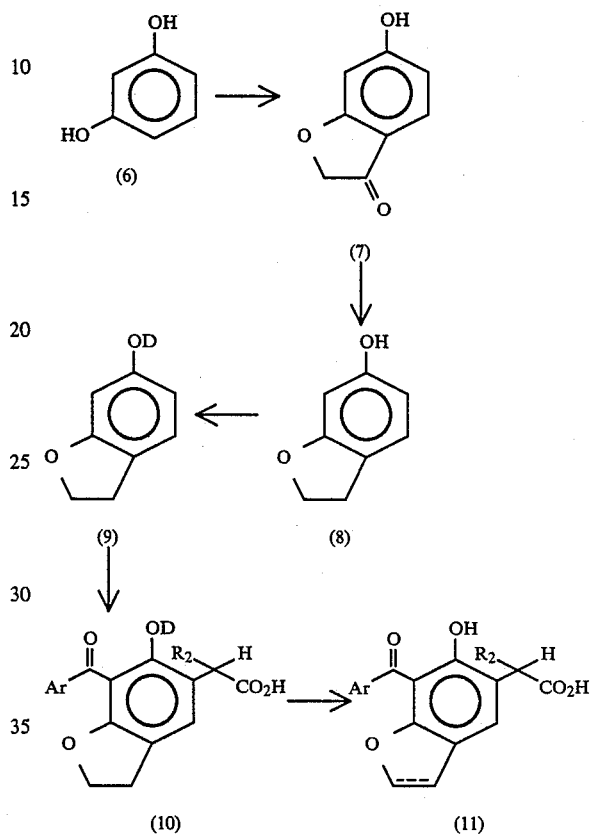

The starting material, resorcinol, is commonly available from a number of chemical firms, for example, Aldrich Chemical Co. or may be prepared by known literature methods. Formula 7, the 6-hydroxycoumaran-3-one, is prepared according to the publication of J. S. H. Davis, et al in J. Chem. Soc., 3206 (1950). Reduction of the 6-hydroxy-coumaran-3-one to give the 6-hydroxy-2,3-dihydrobenzofuran, formula 8, is also carried out in accordance with the foregoing JCS article. The 6-alkoxy-2,3-dihydrobenzofuran (D=lower alkoxy) is prepared by the disclosure in Chemische Berichte, 97 (5) pp. 1252–1255 (1964) authored by Jnanedra Nath Chatterjea and Nagendra Prased, or any other suitable method, such as by the use of alkyl iodides.

The 6-alkoxy-2,3-dihydrobenzofuran is then converted to the 6-alkoxy acid compounds of formula 10 by the process described in Reaction Scheme 4.

The 6-alkoxy compounds of formula 10 are cleaved by acid to give the phenol when the dotted bond is a double bond. Preferably the alkoxy compound will be refluxed in about equal portions of a simple organic acid such as acetic acid and a mineral acid such as hydrobromic acid. The reaction mixture is refluxed for about 30 minutes to 2 hours, preferably about 1 hour, after which the 6-hydroxy product is recovered by extraction or some other appropriate means.

When the -2,3position is saturated or an alkoxy group is present on the aroyl moiety, the 6-position ether is best cleaved by boron trichloride. The boron trichloride cleavage is carried out in an aprotic solvent such as dichloromethane After cooling the solution to between about −10° to +10° C., boron trichloride is added, after which the reaction mixture is allowed to warm to room temperature or thereabouts. After a period of up to 4 hours, preferably 2, the solution is added to water and worked up by means of extraction.

The benzothiophene compounds of this invention are prepared by first making the 2,3-dihydrobenzothiophene starting with thianaphthene according to the steps illstrated in Reaction Scheme 3. The 2,3-dihydrobenzothiophene is then converted to the compounds of Formula I by the sequence of steps set out in Reaction Scheme 4 hereinafter.

REACTION SCHEME 3

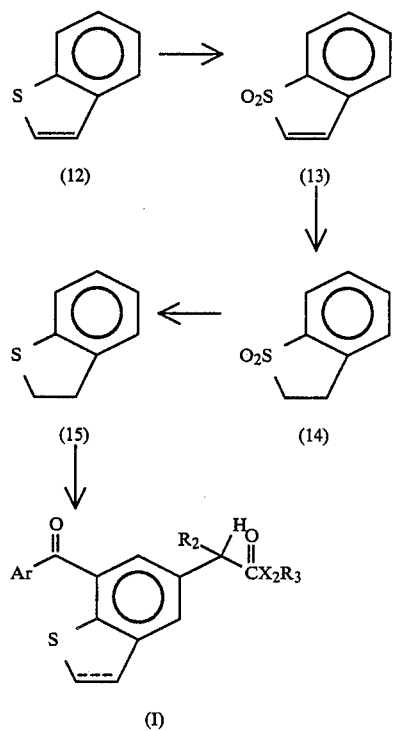

The starting material, thianapthene, is commercially available from Aldrich Chemical Company and others or may be prepared by methods known in the art. In order to effect formation of 2,3-dihydrothianapthene, the dioxide is first prepared via some oxidizing agent. The thianaphthene oxidation is preferably carried out according to F. G. Bordwell, et al., *J. American Chem. Soc.*, Vol. 71, p. 1702 (1949). The thianaphthene is dissolved in a highly polar solvent such as acetic acid to which has been added an oxidizing agent such as, for example, 30% hydrogen peroxide. This mixture is heated at reflux for about 5 to 30 minutes, preferably 15 minutes. The reaction product is then recovered usually by the adding water and collecting the precipitated thianaphthyene-1,1-dioxide.

Reduction of the double bond and subsequent reduction of the dioxide is carried out using the procedure of F. G. Bordwell and McKellin, W. H., *J. Am. Chem. Soc.*, Vol. 73, p. 2251 (1951). The dioxide is dissolved in a polar solvent such as a simple alcohol or a low molecular weight ester, for example, ethyl acetate. A catalytic amount of a transition metal catalyst such as 10% palladium on carbon is added and the solution is shaken under approximately 40 psi of hydrogen until a stoichiometric amount of hydrogen has been taken up.

The dioxide is reduced by a metal hydride such as lithium aluminum hydride. Preferably, the dioxide will be dissolved in a solvent such as tetrahydrofuran and then added dropwise to a solution of the metal hydride in a second solvent such as diethyl ether. After addition of the dioxide is complete, the reaction mixture is heated at reflux for a short period such as, for example, 15 minutes. The reaction mixture is then cooled, water added dropwise and the product recovered by extraction.

Starting with the materials prepared in the three foregoing Reaction Schemes, or with other available appropriate starting material analogous to the 2,3-dihydrobenzofuran and 2,3-dihydrobenzothiophene material, the compound of Formula I are prepared by the following sequence of reactions.

REACTION SCHEME 4

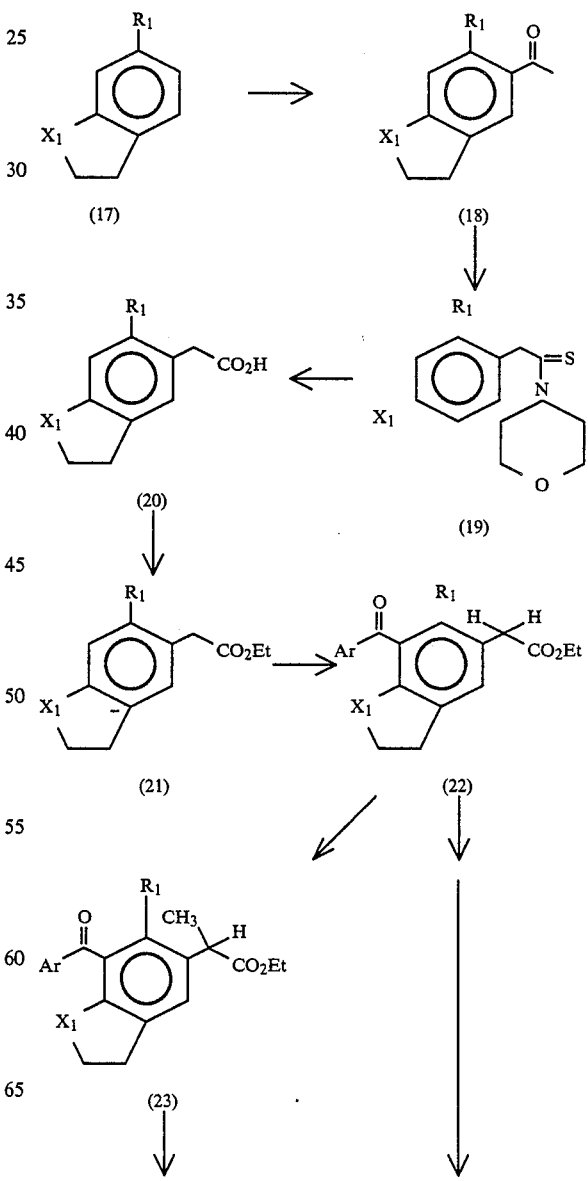

-continued
REACTION SCHEME 4

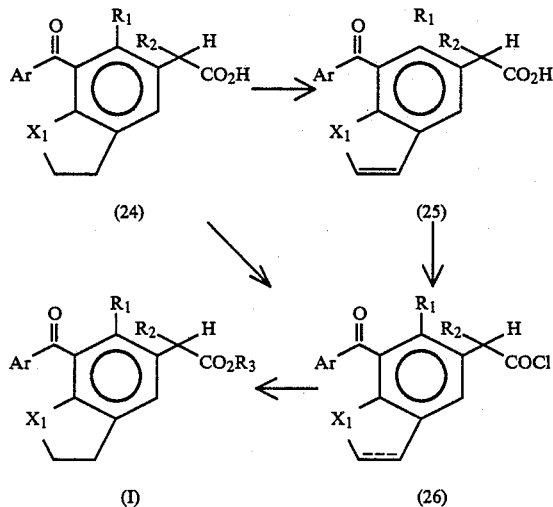

Ar, $R_1$, $R_2$ and $X_1$, are as defined hereinabove.

Addition of an acetyl group to position 5 of 2,3-dihydrobenzofuran, or an analogous structure, is effected by a Friedel-Crafts Reaction employing acetyl chloride and anhydrous aluminum chloride in a solvent such as dichloromethane. The reaction is carried out by slowly adding the acetyl chloride/aluminum chloride solution to 2,3-dihydrobenzofuran dissolved in the same solvent as the added reagents while keeping the temperature between about $-20°$ to $0°$ C., preferably below $-6°$ C. When reagent addition is completed, the reaction mixture is stirred further for about 5 to 20 minutes, preferably 10 minutes, while maintaining the temperature in the same temperature range previosly indicated. The mixture is then added to ice/mineral acid, preferably hydrochloric acid, which solution is then extracted with the reaction solvent.

This 5-acetylbenzofuran is converted to the thioacetic acid morpholide in order to prepare the acetic acid compound of formula 20. The 5-acetylbenzofuran of formula 18 is mixed with morpholine, sulfur, and a catalytic amount of p-toluenesulfonic acid, or the like, and heated at reflux. After about 1 to 5 hours, preferably 3, the reaction mixture is cooled and a simple alcohol such as methanol is added. The morpholide is collected as a precipitate.

Formation of 5-position acetic acid is effected by heating the morpholide at reflux in a solution of acetic acid to which has been added about 15–20% each of sulfuric acid and water The reaction is complete in about 2–4 hours, usually 3 hours.

The acid function is then protected by converting it to an ester, here illustrated as the ethyl ester (formula 21). This is effected by heating the acid at reflux in a non-polar solvent such as toluene and a simple alcohol such as ethanol (about 10%) and a concentrated mineral acid, such as sulfuric acid (about 0.2%) with the azeotropic removal of water The reaction mixture is refluxed for 4–8 hours, preferably about 6 hours.

Addition of the aroyl group at position 7 is effected by a Friedel-Crafts type reaction employing an aroyl acid halide. The benzofuran acetate and aroyl acid halide are first combined in a solvent such as dichloromethane to which is added the catalyst, for example, stannic chloride or the reaction may be carried out in carcon disulfide using aluminum trichloride. The mixture is heated at reflux for about 1 to 5 hours, preferably about 3, cooled, added to water, and extracted with a solvent.

The propionate analog is conveniently prepared at this point by treating the acetate with iodomethane in the presence of a strong base. The reaction is carried out by first preparing a solution of the base, adding this solution to a solution of the acetate, both at reduced temperatures, and then adding the iodomethane.

The base-containing reagent mixture is prepared by adding a strong base such as N-butyl lithium to a dry dipolar aprotic solvent such as tetrahydrofuran at $0°$ C. containing isopropylcyclohexamine. After about 30 minutes this solution is cooled to about $-78°$ C. and added to a solution of the 7-substituted-2,3-dihydrobenzofuran-5-ylacetate in tetrahydrofuran at about $-78°$ C. After another period of about 30 minutes, the iodomethane is added. The temperature is maintained at about $-78°$ C. for approximately another 30 minutes and then allowed to warm to room temperature at which temperature the reaction is allowed to continue for about 1 to 4 hours, preferably about 2 hours. The reaction mixture is then worked up by extraction methods, or the like.

The esters of formulas 22 and 23 are hydrolyzed by base in the presence of a simple alcohol and water, the reaction pot being heated to reflux to effect the reaction. Preferably, the reaction will be carried out in methanol and water with 20% sodium hydroxide. Generally, the reaction is effected in about 1–3 hours, usually about 2 hours. The reaction mixture is then acidified with dilute mineral acid such as hydrochloric acid. The free acid is recovered by extraction or some other appropriate method.

The 2,3-dihydrobenzofuran structure may be converted to the benzofuran by some appropriate dehydrogenation means, such as with n-bromosuccinimide in the presence of a catalytic amount of a peroxide such as benzoyl peroxide, or 2,3-dichloro-5,6-dicyano-1,4-benzoquinone. If the first method is used, the reaction is carried out by dissolving the 2,3-dihydro compound in a halogenated hydrocarbon solvent, or the like, e.g. carbon tetrachloride, containing the n-bromosuccinimide and benzoyl peroxide. This mixture is heated at reflux for between 1–4 hours, preferably 2 hours, after which the reaction product is extracted with an aqueous solution of weak base, such as sodium carbonate. The aqueous extract is then acidifed and the benzofuran extracted with an appropriate organic solvent.

Dehydrogenation using 2,3-dichloro-5,6-dicyano-1,4-benzoquinone (DDQ) is carried out by adding DDQ to a solution of the 2,3-dihydro compound dissolved in a solvent such as dioxane. This solution is heated at reflux for several hours, preferably 1, added to water after being cooled and the product extracted with an appropriate organic solvent.

The following Preparations and Examples illustrate the invention as set out in the preceeding Reaction Schemes but are not intended to limit its scope. Also where necessary, examples are repeated to prepare additional material for subsequent examples; and unless otherwise specified the reactions are carried out at room temperature ($20°$ C. to $30°$ C.).

PREPARATIONS AND EXAMPLES

Preparations 1–4 illustrate the reaction steps set out in Reaction Scheme 1.

Preparation 1

2-Hydroxy-4-methylbenzaldehyde

To a solution of toluene (200 ml) containing cresol (108 g) under a nitrogen atmosphere was added tin tetrachloride (26 g) and tri-N-butylamine (54 g). This mixture was stirred at room temperature for 20 minutes and 66 g of paraformaldehyde added. This solution was then heated at 100° C. for 8 hours. After cooling to room temperature, the reaction mixture was added to water (500 ml) acidifed to pH 2 with hydrochloric acid (2N) and extracted with ether, washed with brine, dried (MgSO$_4$) and evaporated to give 2-hydroxy-4-methylbenzaldehyde, m.p. —60°-61° C.

Preparation 2

3-Hydroxy-6-methyl-2,3-dihydrobenzofuran

To a solution of trimethylsulfoxonium chloride (12.9 g) in tetrahydrofuran (200 ml) was added sodium hydride (2.4 g of 100%). This solution was heated at reflux until hydrogen evolution had ceased. 13.6 g of 2-hydroxy-4-methylbenzaldehyde dissolved in tetrahydrofuran (100 ml) was then added. The reaction mixture was refluxed until the reaction was complete (3 hours). It was then poured into water (600 ml), extracted with ether, the ether dried over sodium sulphate and evaporated to give 3-hydroxy-6-methyl-2,3-dihydrobenzofuran.

Preparation 3

6-Methylbenzofuran

Sulfuric acid (0.2 ml) and 10.0 g of 3-hydroxy6-methyl-2,3-dihydrobenzofuran were dissolved in 200 ml of benzene and heated at reflux with the azeotropic removal of water. After 3 hours, the reaction mixture was added to water (500 ml) and extracted with ether. The combined ether extracts were washed with water and saturated aqueous sodium bicarbonate, dried with sodium sulfate and the solvent evaporated to give 6-methylbenzofuran.

Preparation 4

6-Methyl-2,3-dihydrobenzofuran

6-Methylbenzofuran (15 g) was dissolved in methanol (200 ml) containing 0.5 g of 10% palladium on carbon. This solution was shaken on a Paar hydrogenator under hydrogen at 40 psi. When hydrogen uptake was complete, the solution was filtered through Celite and the ethanol evaporated to yield 6-methyl-2,3-dihydrobenzofuran.

Preparations 5–7 illustrate the reaction steps set out in Reaction Scheme 2.

Preparation 5

6-hydroxycoumaran-3-one

Chloroacetyl chloride (28.25 g) was added dropwise over 1.5 hours to a stirred mixture of resorcinol (Aldrich Chemical Company) (22 g), aluminum chloride (33.3 g) and nitrobenzene (250 cc), the temperature being kept at 50°-55° C. during the chloroacetyl chloride addition and for an additional 15 minutes thereafter. The solution was then cooled and poured into an excess of ice and dilute hydrochloric acid. The organic layer was retained and extracted with aqueous sodium hydroxide (300 ml, 1M). The alkaline extract was acidified with concentrated hydrochloric acid and filtered to give 6-hydroxycoumaran-3-one, m.p. —238°-240° C.

Preparation 6

6-hydroxy-2,3-dihydrobenzofuran 6-hydroxycoumaran-3-one (15 g) was suspended in ethanol (75 ml) and hydrazine hydrate (10 ml, 90%) was added and the mixture heated at reflux for 1 hour. The solvent was evaporated and a solution of potassium hydroxide (15 g) in ethylene glycol (100 ml) was added to the residue. The resulting mixture was distilled with stirring until the internal temperature reached 185°-190° C. This temperature was maintained until no more nitrogen was evolved, approximately 1.5 hours. After cooling, the mixture was added to dilute hydrochloric acid containing sufficient acid to make the mixture acidic. This acidified mixture was then extracted with ether, dried and distilled (110°-120° C./0.75 mm) to give 6-hydroxy-2,3-dihydrobenzofuran.

Preparation 7

6-Methoxy-2,3-dihydrobenzofuran

Dimethylsulfate (35 ml) was added over a period of 3 hours to a stirred solution of 6-hydroxy-2,3-dihydrobenzofuran (12.0 g) dissolved in 200 ml of 10% sodium hydroxide. The solution was stirred for an additional 3 hours after dimethylsulfate addition was completed. The solution was then extracted with ether, the ether extracts combined, dried, and evaporated to give a residue which was distilled (140° C. at 0.5 mm) to yield 6-methoxy-2,3-dihydrobenzofuran.

Proceeding in the same manner, but substituting diethylsulfate, dipropylsulfate, dibutylsulfate, dipentylsulfate, dihexylsulfate, or the like, for dimethylsulfate there are prepared the other 6-alkoxy substituted analogs of 6-methoxy-2,3-dihydrobenzofuran.

Preparations 8–10 illustrate the synthetic steps set out in Reaction Scheme 3.

Preparation 8

Thianaohthene-1,1-dioxide

A solution of 40 grams of thianaphthene (Aldrich Chemical Co.), acetic acid (240 ml) and 30% hydrogen peroxide (180 ml) was heated at reflux for 15 minutes.

This solution was added to water (800 ml), cooled and filtered to give thianaphthene-1,1-dioxide, m.p. —142°-143° C.

Preparation 9

2,3-Dihydrothianaphthene-1,1-dioxide 20 grams of thianaphthene-1-dioxide was dissolved in ethyl acetate (400 ml) containing 0.8 g of 10% palladium on carbon. This solution was shaken on a Paar hydrogenator under 40 psi of hydrogen for 4 hours. The solution was then filtered through Celite and the solvent evaporated to give 2,3-dihydrothianaphthene-1,1-dioxide.

Preparation 10

2,3-Dihydrothianaphthene 2,3-Dihydrothianaphthene-1,1-dioxide (10 g) was dissolved in tetrahydrofuran (100 ml) and added dropwise to a solution of lithium aluminum hydride (10 g) in diethyl ether (250 ml). When addition was complete, the reaction mixture was heated at reflux for 15 minutes When the reaction had cooled to room temperature, water was adde dropwise. The resultant solution was extracted with ether, the combined extracts dried and evaporated to give 2,3-dihydrothianaphthene, b.p. 105°–106° at 13.5 mm.

Preparations 11–16 illustrate the synthetic steps set out in Reaction Scheme 4.

Preparation 11

5-Acetyl-2,3-dihydrobenzofuran

To a solution of 2,3-dihydrobenzofuran (5.0 g) in dichloromethane (30 ml) at −10° C. was slowly added a solution of acetyl chloride (5.9 ml) and anhydrous aluminum chloride (5.5 g) in dichloromethane (30 ml) while keeping the temperature below −6° C. After addition of the 2,3-dihydrobenzofuran was completed, the reaction mixture was stirred for 10 minutes at −10° C. The reaction mixture was then added to an ice/hydrochloric acid mixture which was extracted with dichloromethane. The combined dichloromethane extracts were washed with water and dilute sodium hydroxide, the organic layer dried over sodium sulfate and evaporated. The resulting residue was recrystallized from hexane to give 5-acetyl-2,3-dihydrobenzofuran, m.p.—56°–57° C.

Proceeding in a similar manner, the compounds of Preparations 4, 7 and 10 were converted to the corresponding 5-acetyl compounds as exemplified by the following compounds:
6-methyl-5-acetyl-2,3-dihydrobenzofuran;
6-methoxy-5-acetyl-2,3-dihydrobenzofuran; and
5-acetyl-2,3-dihydrobenzothiophene.

Preparation 12

2,3-Dihydrobenzofuran-5-ylthioacetic Acid Morpholide

Morpholine (1.5 ml), 2,3-dihydro-5-acetylbenzofuran (2.0 g), sulfur (0.395 g) and p-toluene sulfonic acid (0.060 g) were heated at reflux After 3 hours, the reaction mixture was cooled and 6 ml of methanol added. This solution was further cooled which precipitated the morpholide. The precipitate was filtered and washed with cold methanol to give 2,3-dihydrobenzofuran-5-ylthioacetic acid morpholide, m.p. —144°–147° C.

These conditions will convert the other 5-acetyl compounds of Preparation 11 to the corresponding morpholides.

Preparation 13

2,3-Dihydrobenzofuran-5-ylacetic Acid 2,3-dihydrobenzofuran-5-ylthioacetic acid morpholide (5.0 g) was heated at reflux in a solution of acetic acid (20 ml), concentrated sulfuric acid (3.0 ml) and water (4.5 ml). After 3 hours the reaction mixture was cooled and added to water. The product was extracted with ethyl acetate and the combined extracts washed five times with water. The organic solution was then extracted with aqueous saturated sodium bicarbonate solution. The aqueous solution was then acidified and extracted with ethyl acetate. The combined extracts were dried over sodium sulfate and evaporated to give a residue which was recrystallized from acetone/hexane to give 2,3-dihydrobenzofuran-5-ylacetic acid, m.p. —96°–98° C.

Following the same procedure, the other compounds prepared as per Preparation 12 may be converted to the corresponding -5-ylacetic acid.

Preparation 14

Ethyl 2,3-Dihydrobenzofuran-5-ylacetate 2,3-dihydrobenzofuran-5-ylacetic acid (5.4 g) was heated at reflux in a solution of toluene (200 ml), ethanol (20 ml) and concentrated sulfuric acid (0.5 ml) with the azeotropic removal of water. When the reaction was complete, approximately 6 hours, the mixture was added to water/ethyl acetate and extracted with ethyl acetate. The organic extracts were combined and washed with 10% sodium carbonate, dried over sodium sulfate and the solvent evaporated to give the title compound as an oil.

Proceeding similarly, other compounds prepared in Preparation 13 are converted to the ethyl ester or another ester.

EXAMPLE 1

Ethyl 7-(4-Methylthiobenzoyl)-2,3-dihydrobenzofuran-5-yl)acetate

To a solution of ethyl 2,3-dihydrobenzofuran-5-yl-acetate (10.0 g) in dichloromethane (120 ml) and 4-methylthiobenzoyl chloride (9.0 g) was added 12 ml of stannic chloride. This mixture was heated at reflux for approximately 3 hours, cooled and added to water. The aqueous solution was extracted with dichloromethane, the combined extracts washed with water, dried over sodium sulfate and evaporated to give the title product, m.p. 64°–66° C.

Proceeding in a similar manner, but subsituting the appropriate aroyl chloride for 4-methylthiobenzoyl-chloride, there may be prepared corresponding 7-aroyl substituted 2,3-dihydrobenzofuran and 2,3-dihydrobenzothiophene analogs of ethyl 7-(4-methylthiobenzoyl)-2,3-dihydrobenzofuran-5-ylacetate or the alkoxy or alkyl 6-substituted benzofurans from Preparation 14.

EXAMPLE 2

Ethyl d,l-2-(7-(4-Methylthiobenzoyl)-2,3-dihydrobenzofuran-5-yl)propionate

To a solution of isopropylcyclohexylamine (4.15 ml) in dry tetrahydrofuran at 0° C. was added n-butyl lithium (16.6 ml of a 1.6 M solution). After 30 minutes this solution was cooled to −78° C. and added to a solution of ethyl 7-(4-methylthiobenzoyl)-2,3-dihydrobenzofuran-5-ylacetate (9.0 g) in tetrahydrofuran (100 ml) at −78° C. After 30 minutes, 4.0 ml of iodomethane was added to this solution, the temperature being maintained at −78° C. Following a second 30 minute period the solution was allowed to warm to room temperature. After an additional 2 hours at room temperature, the solution was poured into water/ethyl acetate and extracted with ethyl acetate. The combined organic extracts were washed with water, dried over sodium sulfate and, after chromatography, evaporated to give the title compound as an oil.

Using this process all other acetate compounds prepared as per Example 1 are converted to the corresponding propionate.

EXAMPLE 3

7-(4-Methylthiobenzoyl)-2,3-dihydrobenzofuran-5-yl-acetic acid

A solution of ethyl 7-(4-methylthiobenzoyl)-2,3-dihydrobenzofuran-5-ylacetate (10.0 g), 50 ml of methanol, 200 ml of water, and 4 g of sodium hydroxide was heated at reflux for approximately 2 hours. The reaction mixture was cooled and washed with ether. The ether washed aqueous residue was acidified with dilute hydrochloric acid and then extracted with ethyl acetate. The combined organic extracts were washed with water and evaporated to give a residue which was crystallized from acetone/hexane to give 7-(4-methylthiobenzoyl)-2,3-dihydrobenzofuran-5-ylacetic acid, m.p. —150°-152° C.

Proceeding in a similar manner, but substituring for ethyl 7-(4-methylthiobenzoyl)-2,3-dihydrobenzofuran-5-ylacetate, any of the the 2,3-dihydro compounds prepared in Examples 1 and 2 may be converted to the free acid as illustrated by the following compounds:

7-benzoyl-2,3-dihydrobenzofuran-5-ylacetic acid;
7-(4-methoxybenzoyl)-2,3-dihydrobenzofuran-5-ylacetic acid;
7-(4-methylbenzoyl)-2,3-dihydrobenzofuran-5-ylacetic acid;
7-(4-chlorobenzoyl)-2,3-dihydrobenzofuran-5-ylacetic acid;
7-(4-n-hexylbenzoyl)-2,3-dihydrobenzofuran-5-ylacetic acid;
7-(4-hexyloxybenzoyl)-2,3-dihydrobenzofuran-5-ylacetic acid;
7-(4-fluorobenzoyl)-2,3-dihydrobenzofuran-5-ylacetic acid;
7-(2,4,6-trichlorobenzoyl)-2,3-dihydrobenzofuran-5-ylacetic acid;
7-(2,4,6-trimethylbenzoyl)-2,3-dihydrobenzofuran-5-ylacetic acid;
7-(4-methylsulfinylbenzoyl)-2,3-dihydrobenzofuran-5-ylacetic acid;
7-(4-methylsulfonylbenzoyl)-2,3-dihydrobenzofuran-5-ylacetic acid;
7-(fur-2-ylcarbonyl)-2,3-dihydrobenzofuran-5-ylacetic acid;
7-(thiophen-2-ylcarbonyl)-2,3-dihydrobenzofuran-5-ylacetic acid;
7-(fur-3-ylcarbonyl)-2,3-dihydrobenzofuran-5-ylacetic acid;
d,l 2-(7-benzoyl-2,3-dihydrobenzofuran-5-yl)propionic acid;
d,l 2-(7-(4-methoxybenzoyl)-2,3-dihydrobenzofuran-5-yl)propionic acid;
d,l 2-(7-(4-methylbenzoyl)-2,3-dihydrobenzofuran-5-yl)propionic acid;
d,l 2-(7-(4-methylthiobenzoyl)-2,3-dihydrobenzofuran-5-yl)propionic acid;
d,l 2-(7-(4-chlorobenzoyl)-2,3-dihydrobenzofuran-5-yl)propionic acid;
d,l 2-(7-(4-n-hexylbenzoyl)-2,3-dihydrobenzofuran-5-yl)propionic acid;
d,l 2-(7-(4-hexyloxybenzoyl)-2,3-dihydrobenzofuran-5-yl)propionic acid;
d,l 2-(7-(4-fluorobenzoyl)-2,3-dihydrobenzofuran-5-yl)propionic acid;
d,l 2-(7-(2,4,6-trichlorobenzoyl)-2,3-dihydrobenzofuran-5-yl)propionic acid;
d,l 2-(7-(2,4,6-trimethylbenzoyl)-2,3-dihydrobenzofuran-5-yl)propionic acid;
d,l 2-(7-(4-methylsulfinylbenzoyl)-2,3-dihydrobenzofuran-5-yl)propionic acid;
d,l 2-(7-(4-methylsulfonylbenzoyl)-2,3-dihydrobenzofuran-5-yl)propionic acid;
d,l 2-(7-(4-n-butylsulfonylbenzoyl)-2,3-dihydrobenzofuran-5-yl)propionic acid;
d,l 2-(7-(fur-2-ylcarbonyl)-2,3-dihydrobenzofuran-5-yl)propionic acid;
d,l 2-(7-(thien-2-ylcarbonyl)-2,3-dihydrobenzofuran-5-yl)propionic acid;
d,l 2-(7-(fur-3-ylcarbonyl)-2,3-dihydrobenzofuran-5-yl)propionic acid;
d,l 2-(7-(thien-3-ylcarbonyl)-2,3-dihydrobenzofuran-5-yl)propionic acid;
6-methyl-7-benzoyl-2,3-dihydrobenzofuran-5-ylacetic acid;
6-methyl-7-(4-methoxybenzoyl)-2,3-dihydrobenzofuran-5-ylacetic acid;
6-methyl-7-(4-methylbenzoyl)-2,3-dihydrobenzofuran-5-ylacetic acid;
6-methyl-7-(4-chlorobenzoyl)-2,3-dihydrobenzofuran-5ylacetic acid;
6-methyl-7-(4-n-hexylbenzoyl)-2,3-dihydrobenzofuran-5-ylacetic acid;
6-methyl-7-(4-hexoxybenzoyl)-2,3-dihydrobenzofuran-5-ylacetic acid;
6-methyl-7-(4-fluorobenzoyl)-2,3-dihydrobenzofuran-5-ylacetic acid;
6-methyl-7-(2,4,6-trichlorobenzoyl)-2,3-dihydrobenzofuran-5-ylacetic acid;
6-methyl-7-(2,4,6-trimethylbenzoyl)-2,3-dihydrobenzofuran-5-ylacetic acid;
6-methyl-7-(4-methylthiobenzoyl)-2,3-dihydrobenzofuran-5-ylacetic acid;
6-methyl-7-(4-methylsulfinylbenzoyl)-2,3-dihydrobenzofuran-5-ylacetic acid;
6-methyl-7-(4-methylsulfonylbenzoyl)-2,3-dihydrobenzofuran-5-ylacetic acid;
6-methyl-7-(fur-2-ylcarbonyl)-2,3-dihydrobenzofuran-5-ylacetic acid;
6-methyl-7-(thiophen-2-ylcarbonyl)-2,3-dihydrobenzofuran-5-ylacetic acid;
6-methyl-7-(fur-3-ylcarbonyl)-2,3-dihydrobenzofuran-5-ylacetic acid;
6-methyl-7-(thiophen-3-ylcarbonyl)-2,3-dihydrobenzofuran-5-ylacetic acid;
d,l 2-(6-methyl-7-benzoyl-2,3-dihydrobenzofuran-5-yl)propionic acid;
d,l 2-(6-methyl-7-(4-methoxybenzoyl)2,3-dihydrobenzofuran-5-yl)propionic acid;
d,l 2-(6-methyl-7-(4-methylbenzoyl)-2,3-dihydrobenzofuran-5-yl)propionic acid;
d,l 2-(6-methyl-7-(4-chlorobenzoyl)-2,3-dihydrobenzofuran-5-yl)propionic acid;
d,l 2-(6-methyl-7-(4-n-hexylbenzoyl)-2,3-dihydrobenzofuran-5-yl)propionic acid;
d,l 2-(6-methyl-7-(4-hexyloxybenzoyl)-2,3-dihydrobenzofuran-5-yl)propionic acid;
d,l 2-(6-methyl-7-(4-fluorobenzoyl)-2,3-dihydrobenzofuran-5-yl)propionic acid;
d,l 2-(6-methyl-7-(2,4,6-trichlorobenzoyl)-2,3-dihydrobenzofuran-5-yl)propionic acid;
d,l 2-(6-methyl-7-(2,4,6-trimethylbenzoyl)-2,3-dihydrobenzofuran-5-yl)propionic acid;
d,l 2-(6-methyl-7-(4-methylthiobenzoyl)-2,3-dihydrobenzofuran-5-yl)propionic acid;
d,l 2-(6-methyl-7-(4-methylsulfinylbenzoyl)-2,3-dihydrobenzofuran-5-yl)propionic acid;
d,l 2-(6-methyl-7-(4-methylsulfonylbenzoyl)-2,3-dihydrobenzofuran-5-yl)propionic acid;
d,l 2-(6-methyl-7-(fur-2-ylcarbonyl)-2,3-dihydrobenzofuran-5-yl)propionic acid;
d,l 2-(6-methyl-7-(thien-2-ylcarbonyl)-2,3-dihydrobenzofuran-5-yl)propionic acid;

d,l 2-(6-methyl-7-(fur-2-ylcarbonyl)-2,3-dihydrobenzofuran-5-yl)propionic acid;
d,l 2-(6-methyl-7-(thien-2-ylcarbonyl)-2,3-dihydrobenzofuran-5-yl)propionic acid;
6-methoxy-7-benzoyl-2,3-dihydrobenzofuran-5-ylacetic acid;
6-methoxy-7-(4-methoxybenzoyl)-2,3-dihydrobenzofuran-5-ylacetic acid;
6-methoxy-7-(4-methylbenzoyl)-2,3-dihydrobenzofuran-5-ylacetic acid;
6-methoxy-7-(4-chlorobenzoyl)-2,3-dihydrobenzofuran-5-ylacetic acid;
6-methoxy-7-(4-n-hexylbenzoyl)-2,3-dihydrobenzofuran-5-ylacetic acid;
6-methoxy-7-(4-hexyloxybenzoyl)-2,3-dihydrobenzofuran-5-ylacetic acid;
6-methoxy-7-(4-fluorobenzoyl)-2,3-dihydrobenzofuran-5-ylacetic acid;
6-methoxy-7-(2,4,6-trichlorobenzoyl)-2,3-dihydrobenzofuran-5-ylacetic acid;
6-methoxy-7-(2,4,6-trimethylbenzoyl)-2,3-dihydrobenzofuran-5-ylacetic acid;
6-methoxy-7-(4-methylthiobenzoyl)-2,3-dihydrobenzofuran-5-ylacetic acid;
6-methoxy-7-(4-methylsulfinylbenzoyl)-2,3-dihydrobezofuran-5-ylacetic acid;
6-methoxy-7-(4-methylsulfonylbenzoyl)-2,3-dihydrobenzofuran-5-ylacetic acid;
6-methoxy-7-(fur-2-ylcarbonyl)-2,3-dihydrobenzofuran-5-ylacetic acid;
6-methoxy-7-(thiophen-2-ylcarbonyl)-2,3-dihydrobenzofuran-5-ylacetic acid;
6-methoxy-7-(fur-3-ylcarbonyl)-2,3-dihydrobenzofuran-5-ylacetic acid;
6-methoxy-7-(thiophen-3-ylcarbonyl)-2,3-dihydrobenzofuran-5-ylacetic acid;
d,l 2-(6-methoxy-7-benzoyl-2,3-dihydrobenzofuran-5-yl)propionic acid;
d,l 2-(6-methoxy-7-(4-methoxybenzoyl)-2,3-dihydrobenzofuran-5-yl)propionic acid;
d,l 2-(6-methoxy-7-(4-methylbenzoyl)-2,3-dihydrobenzofuran-5-yl)propionic acid;
d,l 2-(6-methoxy-7-(4-chlorobenzoyl)-2,3-dihydrobenzofuran-5-yl)propionic acid;
d,l 2-(6-methoxy-7-(4-n-hexylbenzoyl)-2,3-dihydrobenzofuran-5-yl)propionic acid;
d,l 2-(6-methoxy-7-(4-hexyloxybenzoyl)-2,3-dihydrobenzofuran-5-yl)propionic acid;
d,l 2-(6-methoxy-7-(4-fluorobenzoyl)-2,3-dihydrobenzofuran-5-yl)propionic acid;
d,l 2-(6-methoxy-7-(2,4,6-trichlorobenzoyl)-2,3-dihydrobenzofuran-5-yl)propionic acid;
d,l 2-(6-methoxy-7-(2,4,6-trimethylbenzoyl)-2,3-dihydrobenzofuran-5-yl)propionic acid;
d,l 2-(6-methoxy-7-(4-methylthiobenzoyl)-2,3-dihydrobenzofuran-5-yl)propionic acid;
d,l 2-(6-methoxy-7-(4-methylsulfinylbenzoyl)-2,3-dihydrobenzofuran-5-yl)propionic acid;
d,l 2-(6-methoxy-7-(4-methylsulfonylbenzoyl)-2,3-dihydrobenzofuran-5-yl)propionic acid;
d,l 2-(6-methoxy-7-(fur-2-ylcarbonyl)-2,3-dihydrobenzofuran-5-yl)propionic acid;
d,l 2-(6-methoxy-7-(thien-2-ylcarbonyl)-2,3-dihydrobenzofuran-5-yl)propionic acid;
d,l 2-(6-methoxy-7-(fur-2-ylcarbonyl)-2,3-dihydrobenzofuran-5-yl)propionic acid;
d,l 2-(6-methoxy-7-(thien-2-ylcarbonyl)-2,3-dihydrobenzofuran-5-yl)propionic acid;
7-(4-methoxybenzoyl)-2,3-dihydrobenzothiophen-5-ylacetic acid;
7-(4-methylbenzoyl)-2,3-dihydrobenzothiophen-5-ylacetic acid;
7-(4-chlorobenzoyl)-2,3-dihydrobenzothiophen-5-ylacetic acid;
7-(4-n-hexylbenzoyl)-2,3-dihydrobenzothiophen-5-ylacetic acid;
7-(4-hexyloxybenzoyl)-2,3-dihydrobenzothiophen-5-ylacetic acid;
7-(4-fluorobenzoyl)-2,3-dihydrobenzothiophen-5-ylacetic acid;
7-(2,4,6-trichlorobenzoyl)-2,3-dihydrobenzothiophen-5-ylacetic acid;
7-(2,4,6-trimethylbenzoyl)-2,3-dihydrobenzothiophen-5-ylacetic acid;
7-(4-methylthiobenzoyl)-2,3-dihydrobenzothiophen-5-ylacetic acid;
7-(4-methylsulfinylbenzoyl)-2,3-dihydrobenzothiophen-5-ylacetic acid;
7-(4-methylsulfonylbenzoyl)-2,3-dihydrobenzothiophen-5-ylacetic acid;
7-(fur-2-ylcarbonyl)-2,3-dihydrobenzothiophen-5-ylacetic acid;
7-(thiophen-2-ylcarbonyl)-2,3-dihydrobenzothiophen-5-ylacetic acid;
7-(fur-3-ylcarbonyl)-2,3-dihydrobenzothiophen-5-ylacetic acid;
7-(thiophen-3-ylcarbonyl)-2,3-dihydrobenzothiophen-5-ylacetic acid;
d,l 2-(7-benzoylbenzothiophen-5-yl)propionic acid;
d,l 2-(7-(4-methoxybenzoyl)-2,3-dihydrobenzothiophen-5-yl)propionic acid;
d,l 2-(7-(4-methylbenzoyl)-2,3-dihydrobenzothiophen-5-yl)propionic acid;
d,l 2-(7-(4-chlorobenzoyl)-2,3-dihydrobenzothiophen-5-yl)propionic acid;
d,l 2-(7-(4-n-hexylbenzoyl)-2,3-dihydrobenzothiophen-5-yl)propionic acid;
d,l 2-(7-(4-hexyloxybenzoyl)-2,3-dihydrobenzothiophen-5-yl)propionic acid;
d,l 2-(7-(4-fluorobenzoyl)-2,3-dihydrobenzothiophen-5-yl)propionic acid;
d,l 2-(7-(2,4,6-trichlorobenzoyl)-2,3-dihydrobenzothiophen-5-yl)propionic acid;
d,l 2-(7-(2,4,6-trimethylbenzoyl)-2,3-dihydrobenzothiophen-5-yl)propionic acid;
d,l 2-(7-(4-methylthiobenzoyl)-2,3-dihydrobenzothiophen-5-yl)propionic acid;
d,l 2-(7-(4-methylsulfinylbenzoyl)-2,3-dihydrobenzothiophen-5-yl)propionic acid;
d,l 2-(7-(4-methylsulfonylbenzoyl)-2,3-dihydrobenzothiophen-5-yl)propionic acid;
d,l 2-(7-(fur-2-ylcarbonyl)-2,3-dihydrobenzothiophen-5-yl)propionic acid;
d,l 2-(7-(thien-2-ylcarbonyl)-2,3-dihydrobenzothiophen-5-yl)propionic acid;
d,l 2-(7-(fur-3-ylcarbonyl)-2,3-dihydrobenzothiophen-5-yl)propionic acid; and
d,l 2-(7-(thien-3-ylcarbonyl)-2,3-dihydrobenzothiophen-5-yl)propionic acid.

EXAMPLE 4

7-(4-Methylthiobenzoyl)benzofuran-5-yl)acetic acid a. 7-(4-Methylthiobenzoyl)-2,3-dihydrobenzofuran-5-ylacetic acid (1.0 g) was heated at reflux in carbon tetrachloride (100 ml) containing n-bromosuccinimide (0.54 g) and a catalytic quantity of benzoyl peroxide. After approximately 2 hours the reaction mixture was cooled and extracted with dilute aqueous sodium carbonate. The aqueous extract was acidified with hydrochloric acid, extracted with ethyl acetate, dried and evaporated to yield a residue which was crystallized from acetone/hexane to give (7-(4-methylthiobenzoyl)benzofuran-5-ylacetic acid, m.p. —151°–153° C.

b. 7-(4-Methylbenzoyl)-2,3-dihydrobenzofuran-5-ylacetic acid (1.0 g) was dissolved in dioxane (20 ml). To this was added 2,3-dichloro-5,6-dicyano-1,4-benzoquinone (DDQ) (1.2 g) and the solution heated at reflux for 1 hour. The reaction mixture was added to water and extracted with ethyl acetate, dried with magnesium sulfate and evaporated to dryness. The residue was run on a silica gel column eluting with ethyl acetate/hexane to give ethyl(7-(4-methylbenzoyl)-benzofuran-5-yl) acetate. The acetate was hydrolyzed by the same method set out in Example 3 to give (7-(4-methylbenzoyl)benzofuran-5-yl) acetic acid melting points. This method is especially useful when the 2,3-dihydro starting material contains an alkyl group.

Using one of the two preceeding methods, but substituting for 7-(4-methylthiobenzoyl)benzofuran-5-yl)acetic acid the compounds made as per Example 3, or substituting for 7-(4-methylbenzoyl)benzofuran-5-yl)acetic acid the appropriate 2,3-dihydro compound from Examples 1 and 2, there may be prepared the following compounds:

7-benzoylbenzofuran-5-ylacetic acid;
7-(4-methoxybenzoyl)benzofuran-5-ylacetic acid;
7-(4-chlorobenzoyl)benzofuran-5-ylacetic acid;
7-(4-hexyloxybenzoyl)benzofuran-5-ylacetic acid;
7-(4-fluorobenzoyl)benzofuran-5-ylacetic acid;
7-(2,4,6-trichlorobenzoyl)benzofuran-5-ylacetic acid;
7-(4-methylsulfinylbenzoyl)benzofuran-5-ylacetic acid;
7-(4-methylsulfonylbenzoyl)benzofuran-5-ylacetic acid;
7-(fur-2-ylcarbonyl)benzofuran-5-ylacetic acid;
7-(thien-2-ylcarbonyl)benzofuran-5-ylacetic acid;
7-(fur-3-ylcarbonyl)benzofuran-5-ylacetic acid;
d,l 2-(7-benzoylbenzofuran-5-yl)propionic acid;
d,l 2-(7-(4-methoxybenzoyl)benzofuran-5-yl)propionic acid;
d,l 2-(7-(4-methylthiobenzoyl)benzofuran-5-yl)propionic acid;
d,l 2-(7-(4-chlorobenzoyl)benzofuran-5-yl)propionic acid;
d,l 2-(7-(4-hexyloxybenzoyl)benzofuran-5-yl)propionic acid;
d,l 2-(7-(4-fluorobenzoyl)benzofuran-5-yl)propionic acid;
d,l 2-(7-(2,4,6-trichlorobenzoyl)benzofuran-5-yl)propinic acid;
d,l 2-(7-(4-methylsulfonylbenzoyl)benzofuran-5-yl)propionic acid;
d,l 2-(7-(4-methylsulfinylbenzoyl)benzofuran-5-yl)propionic acid;
d,l 2-(7-(4-n-butylsulfonylbenzoyl)benzofuran-5-yl)propionic acid;
d,l 2-(7-(fur-2-ylcarbonyl)benzofuran-5-yl)propionic acid;
7-(4-methoxybenzoyl)benzothiophen-5-ylacetic acid;
7-(4-chlorobenzoyl)benzothiophen-5-ylacetic acid;
7-(4-hexyloxybenzoyl)benzothiophen-5-ylacetic acid;
7-(4-fluorobenzoyl)benzothiophen-5-ylacetic acid;
7-(2,4,6-trichlorobenzoyl)benzothiophen-5-ylacetic acid;
7-(4-methylthiobenzoyl)benzothiophen-5-ylacetic acid;
7-(4-methylsulfinylbenzoyl)benzothiophen-5-ylacetic acid;
7-(4-methylsulfonylbenzoyl)benzothiophen-5-ylacetic acid;
7-(fur-2-ylcarbonyl)benzothiophen-5-ylacetic acid;
7-(thien-2-ylcarbonyl)benzothiophen-5-ylacetic acid;
7-(fur-3-ylcarbonyl)benzothiophen-5-ylacetic acid;
7-(thien-3-ylcarbonyl)benzothiophen-5-ylacetic acid;
d,l 2-(7-benzoylbenzothiophen-5-yl)propionic acid;
d,l 2-(7-(4-methoxybenzoyl)benzothiophen-5-yl)propionic acid;
d,l 2-(7-(4-chlorobenzoyl)benzothiophen-5-yl)propionic acid;
d,l 2-(7-(4-hexyloxybenzoyl)benzothiophen-5-yl)propionic acid;
d,l 2-(7-(4-fluorobenzoyl)benzothiophen-5-yl)propionic acid;
d,l 2-(7-(2,4,6-trichlorobenzoyl)benzothiophen-5-yl)propionic acid;
d,l 2-(7-(4-methylthiobenzoyl)benzothiophen-5-yl)propionic acid;
d,l 2-(7-(4-methylsulfinylbenzoyl)benzothiophen-5-yl)propionic acid;
d,l 2-(7-(4-methylsulfonylbenzoyl)benzothiophen-5-yl)propionic acid;
d,l 2-(7-(fur-2-ylcarbonyl)benzothiophen-5-yl)propionic acid;
d,l 2-(7-(thien-2-ylcarbonyl)benzothiophen-5-yl)propionic acid;
d,l 2-(7-(fur-3-ylcarbonyl)benzothiophen-5-yl)propionic acid; and
d,l 2-(7-(thien-3-ylcarbonyl)benzothiophen-5-yl)propionic acid.

7-(4-methylbenzoyl)benzofuran-5-ylacetic acid;
7-(4-n-hexylbenzoyl)benzofuran-5-ylacetic acid;
7-(2,4,6-trimethylbenzoyl)benzofuran-5-ylacetic acid;
d,l 2-(7-(4-methylbenzoyl)benzofuran-5-yl)propionic acid;
d,l 2-(7-(4-n-hexylbenzoyl)benzofuran-5-yl)propionic acid;
d,l 2-(7-(2,4,6-trimethylbenzoyl)benzofuran-5-yl)propionic acid;
d,l 2-(7-(thien-2-ylcarbonyl)benzofuran-5-yl)propionic acid;
d,l 2-(7-(fur-3-ylcarbonyl)benzofuran-5-yl)propionic acid;
d,l 2-(7-(thien-3-ylcarbonyl)benzofuran-5-yl)propionic acid;
6-methyl-7-benzoylbenzofuran-5-ylacetic acid;
6-methyl-7-(4-methoxybenzoyl)benzofuran-5-ylacetic acid;
6-methyl-7-(4-methylbenzoyl)benzofuran-5-ylacetic acid;
6-methyl-7-(4-chlorobenzoyl)benzofuran-5-ylacetic acid;
6-methyl-7-(4-n-hexylbenzoyl)benzofuran-5-ylacetic acid;
6-methyl-7-(4-hexyloxybenzoyl)benzofuran-5-ylacetic acid;
6-methyl-7-(4-fluorobenzoyl)benzofuran-5-ylacetic acid;
6-methyl-7-(2,4,6-trichlorobenzoyl)benzofuran-5-yl)acetic acid;
6-methyl-7-(2,4,6-trimethylbenzoyl)benzofuran-5-yl)acetic acid;
6-methyl-7-(4-methylthiobenzoyl)benzofuran-5-yl)acetic acid;

6-methyl-7-(4-methylsulfinylbenzoyl)benzofuran-5-yl)-acetic acid;
6-methyl-7-(4-methylsulfonylbenzoyl)benzofuran-5-yl)acetic acid;
6-methyl-7-(fur-2-ylcarbonyl)benzofuran-5-ylacetic acid;
6-methyl-7-(thien-2-ylcarbonyl)benzofuran-5-yl)acetic acid;
6-methyl-7-(fur-3-ylcarbonyl)benzofuran-5-ylacetic acid;
6-methyl-7-(thien-3-ylcarbonyl)benzofuran-5-yl)acetic acid;
6-methoxy-7-benzoylbenzofuran-5-ylacetic acid;
6-methyoxy-7-(4-methylbenzoyl)benzofuran-5-ylacetic acid;
6-methoxy-7-(4-methylbenzoyl)benzofuran-5ylacetic acid;
6-methoxy-7-(4-chlorobenzoyl)benzofuran-5-ylacetic acid;
6-methoxy-7-(4-n-hexylbenzoyl)benzofuran-5-ylacetic acid;
6-methoxy-7-(4-hexyloxybenzoyl)benzofuran-5-ylacetic acid;
6-methoxy-7-(4-fluorobenzoyl)benzofuran-5-ylacetic acid;
6-methoxy-7-(2,4,6-trichlorobenzoyl)benzofuran-5-yl)acetic acid;
6-methoxy-7-(2,4,6-trimethylbenzoyl)benzofuran-5-yl)acetic acid;
6-methoxy-7-(4-methylthiobenzoyl)benzofuran-5-yl)acetic acid;
6-methoxy-7-(4-methylsulfinylbenzoyl)benzofuran-5-yl)acetic acid;
6-methoxy-7-(4-methylsulfonylbenzoyl)benzofuran-5-yl)acetic acid;
6-methoxy-7-(fur-2-ylcarbonyl)benzofuran-5-ylacetic acid;
6-methoxy-7-(thien-2-ylcarbonyl)benzofuran-5-yl)acetic acid;
6-methoxy-7-(fur-3-ylcarbonyl)benzofuran-5-ylacetic acid;
6-methoxy-7-(thien-3-ylcarbonyl)benzofuran-5-yl)acetic acid;
d,l 2-(6-methoxy-7-benzoyl-benzofuran-5-yl)propionic acid;
d,l 2-(6-methoxy-7-(4-methoxybenzoyl)benzofuran-5-yl)propionic acid;
d,l 2-(6-methoxy-7-(4-methylbenzoyl)benzofuran-5-yl)propionic acid;
d,l 2-(6-methoxy-7-(4-chlorobenzoyl)benzofuran-5-yl)propionic acid;
d,l 2-(6-methoxy-7-(4-n-hexylbenzoyl)benzofuran-5-yl)propionic acid;
d,l 2-(6-methoxy-7-(4-hexyloxybenzoyl)benzofuran-5-yl)propionic acid;
d,l 2-(6-methoxy-7-(4-fluorobenzoyl)benzofuran-5-yl)propionic acid;
d,l 2-(6-methyl-7-(2,4,6-trichlorobenzoyl)benzofuran-5-yl)propionic acid;
d,l 2-(6-methyl-7-(2,4,6-methyltrimethylbenzoyl)benzofuran-5-yl)propionic acid;
d,l 2-(6-methyl-7-(4-methylthiobenzoyl)benzofuran-5-yl)propionic acid;
d,l 2-(6-methyl-7-(4-methylsulfinylbenzoyl)benzofuran-5-yl)propionic acid;
d,l 2-(6-methyl-7-(4-methylsulfonylbenzoyl)benzofuran-5-yl)propionic acid;
d,l 2-(6-methyl-7-(fur-2-ylcarbonyl)benzofuran-5-yl)propionic acid;
d,l 2-(6-methyl-7-(thien-2-ylcarbonyl)benzofuran-5-yl)propionic acid;
d,l 2-(6-methyl-7-(fur-2-ylcarbonyl)benzofuran-5-yl)propionic acid;
d,l 2-(6-methyl-7-(thien-2-ylcarbonyl)benzofuran-5yl)-propionic acid;
7-(2,4,6-trimethylbenzoyl)benzothiophen-5-ylacetic acid;
7-(4methylbenzobenzoyl)benzothiophen-5-ylacetic acid;
7-(4-n-hexylbenzoyl)benzothiophen-5-ylacetic acid
d,l 2-(7-(4-methylbenzoyl)benzothiophen-5-yl)propionic acid;
d,l 2-(7-(4-n-hexylbenzoyl)benzothiophen-5-yl)propionic acid; and
d,l 2-(7-(2,4,6-trimethylbenzoyl)benzothiophen-5-yl)propionic acid.

EXAMPLE 5

6-Hydroxy-7-benzoylbenzofuran-5-ylacetic acid a. 6-Methoxy-7-benzoylbenzofuran-5-ylacetic acid (5.0 g) was heated at reflux in a mixture of acetic acid (50 ml) and 48% hydrobromic acid (50 ml). After the reaction was completed, approximately 1 hour, the cooled solution was added to 400 ml of water which was then extracted with ethyl acetate. The combined organic extracts were washed four times with water, dried with sodium sulfate and evaporated to give 6-hydroxy-7-benzoylbenzofuran-5-ylacetic acid.

b. Ethyl 6methoxy-7-(4-methozybenzoyl)-2,3-dihydrobenzofuran-5-ylacetate (3.6 g) was dissolved in dichloromethane (40 ml) and cooled to 0° C. To this was added boron trichloride (30 ml 1M). The reaction was allowed to warm to room temperature and, after 2 hours, added to water. The dichloromethane solution was washed 2 times with water, dried, and evaporated. The residue was run on a silica gel column, being eluted with ethyl acetate/hexane to give ethyl 6-hydroxy-7-(4-methoxybenzoyl)-2,3-dihydrobenzofuran-5-ylacetate. Saponification as per Example 3 gave 6-hydroxy-7-(4-methylbenzoyl)-2,3-dihydrobenzofuran-5-ylacetic acid.

Proceeding according to either method (a) or (b), the 6-alkoxy compounds of Examples 3 and 4 are converted to their corresponding hydroxy compound as exemplified by the following compounds:
6-hydroxy-7-benzoylbenzofuran-5-ylacetic acid;
6-hydroxy-7-(4-methybenzoyl)benzofuran-5-ylacetic acid;
6-hydroxy-7-(4-chlorobenzoyl)benzofuran-5-ylacetic acid;
6-hydroxy-7-(4-n-hexylbenzoyl)benzofuran-5-ylacetic acid;
6-hydroxy-7-(4-fluorobenzoyl)benzofuran-5-ylacetic acid;
6-hydroxy-7-(2,4,6-trichlorobenzoyl)benzofuran-5-yl) acetic acid;
6-hydroxy-7-(2,4,6-trimethylbenzoyl)benzofuran-5-yl)acetic acid;
6-hydroxy-7-(4-methylthiobenzoyl)benzofuran-5-yl)acetic acid;
6-hydroxy-7-(4-methylsulfinylbenzoyl)benzofuran-5-ylacetic acid;
6-hydroxy-7-(4-methylsulfonylbenzoyl)benzofuran-5-ylacetic acid;

6-hydroxy-7-(fur-2-ylcarbonyl)benzofuran-5-ylacetic acid;
6-hydroxy-7-(thien-2-ylcarbonyl)benzofuran-5-ylacetic acid;
6-hydroxy-7-(fur-3-ylcarbonyl)benzofuran-5-ylacetic acid;
6-hydroxy-7-(thien-3-ylcarbonyl)benzofuran-5-ylacetic acid;
d,l 2-(6-hydroxy-7-benzoylbenzofuran-5-yl)propionic acid;
d,l 2-(6-hydroxy-7-(4-methylbenzoyl)benzofuran-5-yl)propionic acid;
d,l 2-(6-hydroxy-7-(4-chlorobenzoyl)benzofuran-5-yl)propionic acid;
d,l 2-(6-hydroxy-7-(4-n-hexyloxybenzoyl)benzofuran-5-yl)propionic acid;
d,l 2-(6-hydroxy-7-(4-fluorobenzoyl)benzofuran-5-yl)propionic acid;
d,l 2-(6-hydroxy-7-(2,4,6-trichlorobenzoyl)benzofuran-5-yl)propionic acid;
d,l 2-(6-hydroxy-7-(2,4,6-trimethylbenzoyl)benzofuran-5-yl)propionic acid;
d,l 2-(6-hydroxy-7-(4-methylthiobenzoyl)benzofuran-5-yl)propionic acid;
d,l 2-(6-hydroxy-7-(4-methylsulfinylbenzoyl)benzofuran-5-yl)propionic acid;
d,l 2-(6-hydroxy-7-(4-methylsulfonylbenzoyl)benzofuran-5-yl)propionic acid;
d,l 2-(6-hydroxy-7-(4-n-butylsulfonylbenzoyl)benzofuran-5-yl)propionic acid;
d,l 2-(6-hydroxy-7-(fur-2-ylcarbonyl)benzofuran-5-yl)propionic acid;
d,l 2-(6-hydroxy-7-(thien-2-ylcarbonyl)benzofuran-5-yl)propionic acid;
d,l 2-(6-hydroxy-7-(fur-2-ylcarbonyl)benzofuran-5-yl)propionic acid;
d,l 2-(6-hydroxy-7-(thien-2-ylcarbonyl)benzofuran-5-yl)propionic acid;
6-hydroxy-7-benzoyl-2,3-dihydrobenzofuran-5-ylacetic acid;
6-hydroxy-7-(4-methylbenzoyl)-2,3-dihydrobenzofuran-5-ylacetic acid;
6-hydroxy-7-(4-chlorobenzoyl)-2,3-dihydrobenzofuran-5-ylacetic acid;
6-hydroxy-7-(4-n-hexyloxybenzoyl)-2,3-dihydrobenzofuran-5-ylacetic acid;
6-hydroxy-7-(4-fluorobenzoyl)-2,3-dihydrobenzofuran-5-ylacetic acid;
6-hydroxy-7-(2,4,6-trichlorobenzoyl)-2,3-dihydrobenzofuran-5-ylacetic acid;
6-hydroxy-7-(2,4,6-trimethylbenzoyl)-2,3-dihydrobenzofuran-5-ylacetic acid;
6-hydroxy-7-(4-methylthiobenzoyl)-2,3-dihydrobenzofuran-5-ylacetic acid;
6-hydroxy-7-(4-methylsulfinylbenzoyl)-2,3-dihydrobenzofuran-5-ylacetic acid;
6-hydroxy-7-(4-methylsulfonylbenzoyl)-2,3-dihydrobenzofuran-5-ylacetic acid;
6-hydroxy-7-(fur-2-ylcarbonyl)-2,3-dihydrobenzofuran-5-ylacetic acid;
6-hydroxy-7-(thien-2-ylcarbonyl)-2,3-dihydrobenzofuran-5-ylacetic acid;
6-hydroxy-7-(fur-3-ylcarbonyl)-2,3-dihydrobenzofuran-5-ylacetic acid;
6-hydroxy-7-(thien-3-ylcarbonyl)-2,3-dihydrobenzofuran-5-ylacetic acid;
d,l 2-(6-hydroxy-7-benzoyl-2,3-dihydrobenzofuran-5-yl)propionic acid;
d,l 2-(6-hydroxy-7-(4-methylbenzoyl)-2,3-dihydrobenzofuran-5-yl)propionic acid;
d,l 2-(6-hydroxy-7-(4-chlorobenzoyl)-2,3-dihydrobenzofuran-5-yl)propionic acid;
d,l 2-(6-hydroxy-7-(4-n-hexyloxybenzoyl)-2,3-dihydrobenzofuran-5-yl)propionic acid;
d,l 2-(6-hydroxy-7-(4-fluorobenzoyl)-2,3-dihydrobenzofuran-5-yl)propionic acid;
d,l 2-(6-hydroxy-7-(2,4,6-trichlorobenzoyl)-2,3-dihydrobenzofuran-5-yl)propionic acid;
d,l 2-(6-hydroxy-7-(2,4,6-trimethylbenzoyl)-2,3-dihydrobenzofuran-5-yl)propionic acid;
d,l 2-(6-hydroxy-7-(4-methylthiobenzoyl)-2,3-dihydrobenzofuran-5-yl)propionic acid;
d,l 2-(6-hydroxy-7-(4-methylsulfinylbenzoyl)-2,3-dihydrobenzofuran-5-yl)propionic acid;
d,l 2-(6-hydroxy-7-(4-methylsulfonylbenzoyl)-2,3-dihydrobenzofuran-5-yl)propionic acid;
d,l 2-(6-hydroxy-7-(4-n-butylsulfonylbenzoyl)-2,3-dihydrobenzofuran-5-yl)propionic acid;
d,l 2-(6-hydroxy-7-(fur-2-ylcarbonyl)-2,3-dihydrobenzofuran-5-yl)propionic acid;
d,l 2-(6-hydroxy-7-(thien-2-ylcarbonyl)-2,3-dihydrobenzofuran-5-yl)propionic acid;
d,l 2-(6-hydroxy-7-(fur-2-ylcarbonyl)-2,3-dihydrobenzofuran-5-yl)propionic acid; and
d,l 2-(6-hydroxy-7-(thien-2-ylcarbonyl)-2,3-dihydrobenzofuran-5-yl)propionic acid.

EXAMPLE 6

7-(4-Methylthiobenzyl)benzofuran-5-ylacetyl Chloride

A solution of 7-(4-methylthiobenzyl)benzofuran-5-ylacetic acid (10 g), dichloromethane (100 ml), thionyl chloride (10.0 ml) and dimethylformamide (0.2 ml) was stirred at room temperature for 6 hours. The solvent was then evaporated to give a residue which contained the title compound.

Proceeding in the same manner, all the acids of Examples 3, 4 and 5 are converted to their corresponding acid chloride.

EXAMPLE 7

2-Propen-1-yl 7-(4-methylthiobenzoyl)benzofuran-5-ylacetate

Allyl alcohol (2.0 ml) was added to a solution of 7-(4-methylthiobenzoyl)-2,3-dihydrobenzofuran-5-ylacetyl chloride (2.0 g) in acetonitrile (100 ml) and triethylamine (2.0 ml). This solution was stirred at room temperature for 12 hours. The solvent was then evaporated to dryness and the residue was taken up in a solution of ethyl acetate/water, washed 3 times with water, the ethyl acetate dried and evaporated to dryness after which the residue was purified by chromatography.

Using this same procedure, any of the acid halides prepared as per Examples 8 are converted to the 2-propen-1-yl ester.

EXAMPLE 8

2,2-Dimethyl-1,3-dioxolan-4-yl-methyl(7-(4methylthiobenzoyl)benzofuran-5-yl)acetate A solution of 7-(4-methylthiobenzoyl)benzofuran-5-ylacetyl chloride, 75 ml of tetrahydrofuran, 8.0 ml of 2,2-dimethyl-1,3-dioxolane-4-methanol and 8.0 ml of pyridine was stirred at room temperature for 4 days. The reaction mixture was then added to ether/water, extracted with ether which was washed 6 times with water. The ether was dried and evaporated after which the residue was separated on silicia gel.

All other acetyl or propionyl chloride compounds prepared in Example 8 may be converted to the 2,2-dimethyl-1,3-dioxolan-4-ylmethyl ester. Also, by substitution of another 2,2-dilower alkyl-1,3-dioxolane-4-ylmethanol compound for the 2,2-dimethyl-1,3-dioxolane-4-methanol, there may be prepared the other compounds of this invention wherein R is lower alkyl.

EXAMPLE 9

2,3-Dihydroxypropan-1-yl 7-(4-Methylthiobenzoyl)benzofuran-5-yl)acetate

To a solution of 2,2-dimethyl-1,3-dioxolane-4-ylmethyl 7-(4-methylthiobenzoyl)benzofuran-5-ylacetate (1.5 g) in 30 ml of acetone was added 10% hydrochloric acid (10 ml) and stirred at room temperature for 12 hours. This solution was then added to a solution of ether/water, extracted with ether, washed 6 times with water, dried and evaporated and after silica gel chromatography gave the title compound.

Proceeding in a similar manner, but substituting the appropriate 2,2-dialkyl-1,3-dioxolan-4-ylmethyl compound from Example 8 for the title compound, there are prepared the 2,3-dihydroxypropan-1-yl esters of the present invention.

EXAMPLE 10

Isoamyl 7-(4-methoxybenzoyl)-benzofuran-5-ylacetate

A solution of 300 mg of 7-(4-methoxybenzoyl)-benzofuran-5-ylacetic acid in 5 ml of isoamyl alcohol is saturated with hydrogen chloride. After 24 hours, the excess alcohol is distilled off in vacuo and the residue purified by chromatography on silica gel to yield isoamyl (7-(4-methoxybenzoyl)benzofuran-5-ylacetate. Likewise, other esters, e.g. pentyl, hexyl, octyl, nonyl, dodecyl, and the like, are obtained by substituting other alcohols, e.g., pentyl, hexyl, octyl, nonyl, dodecyl alcohol, and the like, for isoamyl alcohol.

By the same method the free acid compounds obtained in Examples 3, 4, 5 and 6 are esterified with the appropriate alcohol thus obtaining the corresponding esters.

EXAMPLE 11

Sodium 7-(4-chlorobenzoyl)benzofuran-5-ylacetate

To a solution of 250 mg of (7-(4-chlorobenzoyl)benzofuran-5-ylacetic acid in 5 ml of methanol is added 1 molar equivalent of sodium hydroxide in the form of 0.1 N solution. The solvent is evaporated to dryness and the residue taken up in 2 ml of methanol, followed by precipitation with ether, to yield sodium 7-(4-chlorobenzoyl)benzofuran-5-ylacetate.

Likewise, other salts, e.g., ammonium and potassium salts of 7-(4-chlorobenzoyl)benzofuran-5-ylacetic acid are prepared by substituting ammonium hydroxide and potassium hydroxide for sodium hydroxide.

In a similar manner, the other acetic and propionic acid compounds obtained in Examples 3, 4 and 5 can be converted into the corresponding sodium, potassium and ammonium salts.

EXAMPLE 12

Calcium 7-benzoylbenzofuran-5-ylacetate

To a solution of 200 mg of 7-benzoylbenzofuran-5-ylacetic acid in 5 ml of methanol is added a 1 molar equivalent of potassium hydroxide in the form of a 0.1 N solution, thus, yielding a solution containing potassium 7-benzoylbenzofuran-5-ylacetate. A solution of 60 mg of calcium carbonate dissolved in the minimum amount of 1 N hydrochloric acid necessary to effect solution of the calcium carbonate is bufered with 150 mg of solid ammonium chloride followed by the addition of 5 ml of water. The thus obtained buffered calcium solution is then added to the solution of potassium 7-benzoylbenzofuran-5-ylacetate and the precipitate which forms is collected by filtration, washed with water and air dried to yield calcium 7-benzoylbenzofuran-5-ylacetate.

Likewise, magnesium 7-benzoylbenzofuran-5-ylacetate is prepared by substituting magnesium carbonate for calcium carbonate.

Similarly, by substituting other carboxylic acids of Examples 3, 4 and 5 for 7-benzoylbenzofuran-5-ylacetic acid there are obtained the corresponding calcium and magnesium salts.

EXAMPLE 13

Copper 7-(4-methoxybenzoyl)-benzofuran-5-ylacetate

To a solution of 200 mg of 7-(4-methoxybenzoyl)-benzofuran-5-ylacetic acid in 5 ml of methanol is added a 1 Molar equivalent of potassium hydroxide in the form of 0.1 N solution. The solvent is stripped and the residue is dissolved in 5 ml of water. The thus obtained aqueous solution of potassium 7-(4-methoxybenzoyl)-benzofuran-5-ylacetate is added to a solution of 150 mg of cupric nitrate trihydrate in 5 ml of water. The formed precipitate is collected, washed with water and air dried, thus obtaining copper 7-(4-methoxybenzoyl)-benzofuran-5-ylacetate.

In a similar manner, the free acid compounds obtained in Examles 3, 4 and 5 can be converted into the corresponding copper salts.

EXAMPLE 14

Isooropylamine 7-(4-methylthiobenzoyl)benzofuran-5-ylacetate

A solution of 200 mg of (7-(4-methylthiobenzoyl)-benzofuran-5-ylacetic acid in 15 ml of hot benzene is treated with 60 mg of isopropylamine. The solution is allowed to cool to room temperature and the product filtered off, washed with ether and dried to yield the isopropylamine salt of 7-(4-methylthiobenzoyl)benzofuran-5-ylacetic acid.

Likewise, other amine salts, e.g., diethylamine, ethanolamine, piperidine, tromethamine, choline and caffeine salts of 7-(4-methylthiobenzoyl)benzofuran-5-ylacetic acid are prepared by substituting each of the respective amines for isopropylamine.

In a similar manner, the free acid compound obtained in Examples 3, 4 and 5 can be converted into the corresponding isopropylamine, diethylamine, ethanolamine, piperidine, tromethamine, choline and caffeine salts.

EXAMPLE 15

Methyl d,l 2-(7-benzoylbenzofuran-5-yl)propionate

A solution of 200 mg of d,l 2-(7-benzoylbenzofuran-5yl) propionic acid in 5 ml of dichloromethane is treated with an excess of ethereal diazomethane, and the reaction mixture is maintained at room temperature for 30 minutes. Solvent and excess reagent are eliminated under reduced pressure and the residue crystallized from ethyl acetate/methanol to yield methyl d,l 2-(7-benzoylbenzofuran-5-yl)propionate.

Likewise, but using diazoethane, diazopropane and diazobutane in place of diazomethane, there are, respectively, obtained
ethyl d,l 2-(7-benzoylbenzofuran-5-yl)propionate;
propyl d,l 2-(7-benzoylbenzofuran-5-yl)propionate; and
butyl d,l 2-(7-benzoylbenzofuran-5-yl)propionate.

In a similar manner, the acids obtained in Examples 3, 4 and 5 are converted into the corresponding methyl, ethyl, propyl and butyl esters.

EXAMPLE 16

| Ingredients | Quantity per tablet, mgs. |
|---|---|
| d,l 2-(7-benzoylbenzofuran)propionic acid | 25 |
| cornstarch | 20 |
| lactose, spray-dried | 153 |
| magnesium stearate | 2 |

The above ingredients are thoroughly mixed and pressed into sinlge scored tablets.

EXAMPLE 17

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 18

| Ingredients | Quantity per tablet, mgs. |
|---|---|
| Active ingredient | 200 |
| cornstarch | 50 |
| lactose | 145 |
| magnesium stearate | 5 |

The above ingredients are mixed intimately and pressed into single scored tablets.

EXAMPLE 19

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE 20

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 21

Topical Formulation

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water q.s. | 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 22

A suppository totalling 2.5 grams is prepared having the following composition:

7-(methylthiobenzoyl)benzofuran-5-yl acetic acid, 25 mg; witepsol H-15 (triglycerides of saturated vegetable fatty acid; a product of Riches-Nelson, Inc., New York, N.Y.) balance.

EXAMPLE 23

Screening Test for Anti-inflammatory Activity

The oral anti-inflammatory activity is determined utilizing carrageenin induced paw inflammation in the rat in accordance with the method of Winter, et al., *Pro. Soc. Exp. Biol. Med.*, III:544–547, (1962)

Materials and Methods

Female rats weighing 80–90 grams are used. The test materials are given at hour 0 orally by gavage in 1 ml of aqueous vehicle. At hour 1, 0.05 ml of a 1% solution (in 0.9% NaCl) of carrageenin is injected into the right hind 5 paw. This injection causes inflammation of the paw. The rats are sacrificed at hour 4, at which time both hind paws are removed and weighed separately.

End Point

The percent increase in paw size is calculated as follows:

$$\frac{\text{Wt of right paw} - \text{Wt of left paw}}{\text{Wt of right paw}} \times 100$$

The smaller the percent increase in paw size, the lesser the degree of inflammation and the greater the anti-inflammatory activity.

Compounds of this invention show anti-inflammatory activity in this test.

EXAMPLE 24

Screening test for analgetic activity

The oral analgetic activity potential is determined utilizing the mouse analgetic (anti-writhing) assay in accordance with the method of Hendershot & Forsaith, *J. Pharmacol. Exp. Ther.*, 125:237–240, (1959).

Materials & Methods

The test material is administered orally by gavage in an aqueous vehicle at time 0 to 18–20 gram male Swiss-Webster mice. Twenty minutes later 0.5 ml of a 0.02% solution of phenylquinone is injected IP. This solution induces writhing.

End Point

The total number of mice that writhe and the average number of writhes per mouse indicates the activity of the compound tested; the fewer writhes per mouse indicates a greater activity. Compounds of this invention show analgetic activity in this assay.

The subject matter claimed is:

1. A compound selected from those represented by the formula:

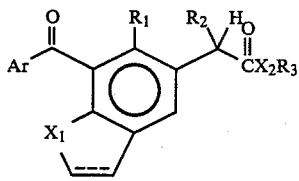

or a pharmaceutically acceptable salt wherein:
   $R_1$ is hydrogen, hydroxy, lower alkoxy, or methyl;
   $R_2$ is hydrogen or methyl;
   $R_3$ is hydrogen, alkyl, phenyl, phenyl lower alkyl, 2-furyl, 3-furyl, 2-thienyl, 3-thienyl,

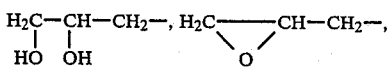

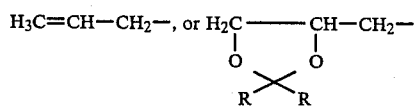

wherein the R groups are the same and are lower alkyl;
   $X_1$ is oxygen or is sulfur if $R_1$ is hydrogen
   $X_2$ is oxygen or sulfur;
   Ar is phenyl unsubstituted or independently substituted with one or more substituents which are lower alkyl, lower alkoxy, halo, lower alkyl sulfinyl, lower alkyl sulfonyl, lower alkyl thio, or 2-furyl, 3-furyl, 2-thienyl, or 3-thienyl; and the dotted line represents a single or double bond.

2. A compound of claim 1 wherein $X_1$ is oxygen.

3. The compound of claim 2 wherein Ar is phenyl unsubstituted or substituted with one or more substituents which are lower alkyl, lower alkoxy, halo, lower alkyl thio, lower alkyl sulfinyl, or lower alkyl sulfonyl.

4. A compound according to claim 3 wherein $R_1$ is hydrogen.

5. A compound according to claim 4 wherein Ar is unsubstituted phenyl.

6. A compound according to claim 5 which is 7-benzoylbenzofuran-5-ylacetic acid.

7. A compound according to claim 5 which is d,l-2-(7-benzoylbenzofuran-5-yl)propionic acid.

8. A compound according to claim 4 wherein Ar is substituted phenyl.

9. A compound according to claim 7 which is 7-(4-methylthiobenzoyl)benzofuran-5-ylacetic acid.

10. A compound according to claim 7 which is 7-(4-chlorobenzoyl)benzofuran-5-ylacetic acid.

11. A compound according to claim 7 which is d,l-2-(7-(4-methylthiobenzoyl)benzofuran-5-yl)propionic acid.

12. A compound according to claim 7 which is d,l-2-(7-(4-chlorobenzoyl)benzofuran-5-yl)propionic acid.

13. A compound according to claim 1 wherein $X_1$ is sulfur.

14. A compound according to claim 10 wherein Ar is phenyl unsubstituted or substituted with 1 or more substituents which are lower alkyl, lower alkoxy, halo, lower alkyl thio, lower alkyl sulfinyl, or lower alkyl sulfonyl.

15. A composition for treating pain, inflammation, or pyrexia in mammals comprising a pharmaceutically acceptable non-toxic excipient and a therapeutically effective amount of a compound of claim 1.

16. A method of treating pain, inflammation, or pyrexia in mammals which comprises administering to a mammal suffering therewith a therapeutically effective amount of a compound of claim 1.

* * * * *